(12) United States Patent
Rossi et al.

(10) Patent No.: US 11,407,218 B2
(45) Date of Patent: Aug. 9, 2022

(54) IDENTIFYING RANDOM BITS IN CONTROL DATA PACKETS

(71) Applicant: HEWLETT-PACKARD DEVELOPMENT COMPANY, L.P., Spring, TX (US)

(72) Inventors: John Rossi, Vancouver, WA (US); Scott A. Linn, Corvallis, OR (US); James Michael Gardner, Corvallis, OR (US); Erik D. Ness, Vancouver, WA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 169 days.

(21) Appl. No.: 16/769,396

(22) PCT Filed: Feb. 6, 2019

(86) PCT No.: PCT/US2019/016739
§ 371 (c)(1),
(2) Date: Jun. 3, 2020

(87) PCT Pub. No.: WO2020/162898
PCT Pub. Date: Aug. 13, 2020

(65) Prior Publication Data
US 2021/0229430 A1 Jul. 29, 2021

(51) Int. Cl.
*B41J 2/045* (2006.01)
*G06F 3/12* (2006.01)

(52) U.S. Cl.
CPC ....... *B41J 2/04543* (2013.01); *B41J 2/04586* (2013.01); *G06F 3/1206* (2013.01);
(Continued)

(58) Field of Classification Search
CPC ................ B41J 2/04536; B41J 2/04541; B41J 2/04543; B41J 2/04586; G06F 3/1206;
(Continued)

(56) References Cited

U.S. PATENT DOCUMENTS 4,026,402 A  5/1977  Byrd
4,872,028 A  10/1989  Lloyd
(Continued)

FOREIGN PATENT DOCUMENTS

CN  1727186 A  2/2006
CN  1922019 A  2/2007
(Continued)

OTHER PUBLICATIONS

Hewlett-Packard Development Company, L.P., Int. Appl. No. PCT/US2019/016735 entitled Issue Determinations Responsive to Measurements filed Feb. 6, 2019 (29 pages).
(Continued)

*Primary Examiner* — Thinh H Nguyen
(74) *Attorney, Agent, or Firm* — Dicke Billig & Czaja PLLC

(57) ABSTRACT

A fluid ejection controller interface includes input logic to receive control data packets and a first clock signal, each control data packet including a set of primitive data bits and a set of random bits, wherein the input logic identifies the random bits in the received control data packets to facilitate the creation of modified control data packets. The fluid ejection controller interface includes a clock signal generator to generate a second clock signal that is different than the first clock signal, and output logic to receive the modified control data packets, and output the modified control data packets to a fluid ejection controller of a fluid ejection device based on the second clock signal.

20 Claims, 8 Drawing Sheets

(52) U.S. Cl.
CPC .......... *G06F 3/1211* (2013.01); *G06F 3/1229* (2013.01); *G06F 3/1285* (2013.01)

(58) Field of Classification Search
CPC .... G06F 3/1211; G06F 3/1229; G06F 3/1285; G11C 16/10; G11C 16/26
See application file for complete search history.

(56) References Cited

U.S. PATENT DOCUMENTS

| | | |
|---|---|---|
| 5,422,662 A | 6/1995 | Fukushima et al. |
| 5,541,629 A | 7/1996 | Saunders |
| 5,751,302 A | 5/1998 | Rezanka |
| 5,917,509 A * | 6/1999 | Becerra ............... B41J 2/04598 347/11 |
| 6,176,569 B1 | 1/2001 | Anderson et al. |
| 6,302,507 B1 | 10/2001 | Prakash et al. |
| 6,616,256 B1 | 9/2003 | Cook |
| 6,698,862 B1 | 3/2004 | Choi et al. |
| 7,104,624 B2 * | 9/2006 | Schloeman ............ B41J 2/145 347/180 |
| 7,159,959 B2 | 1/2007 | Schremp et al. |
| 7,419,236 B2 | 9/2008 | Masuda |
| 7,578,569 B2 | 8/2009 | Silverbrook |
| 7,738,137 B2 | 6/2010 | Graf et al. |
| 7,758,141 B2 | 7/2010 | Sakurai |
| 7,866,778 B2 | 1/2011 | Silverbrook et al. |
| 7,976,115 B2 | 7/2011 | Gibson et al. |
| 8,199,342 B2 | 6/2012 | Martin |
| 8,348,373 B2 | 1/2013 | Martin et al. |
| 8,353,567 B1 | 1/2013 | Banerjee et al. |
| 8,556,364 B2 | 10/2013 | Hoisington et al. |
| 8,777,364 B2 | 7/2014 | Carrobe et al. |
| 8,864,260 B1 | 10/2014 | Ge |
| 9,415,585 B1 | 8/2016 | Goyen et al. |
| 9,597,894 B2 | 3/2017 | Buxton et al. |
| 9,776,395 B2 | 10/2017 | Anderson et al. |
| 2004/0104973 A1 | 6/2004 | Huang |
| 2004/0183842 A1 | 9/2004 | Kobayashi |
| 2005/0110814 A1 | 5/2005 | Imai |
| 2005/0190217 A1 | 9/2005 | Wade |
| 2006/0092437 A1 | 5/2006 | Martin |
| 2006/0109296 A1 | 5/2006 | Shamoun et al. |
| 2007/0095928 A1 | 5/2007 | Balinsky |
| 2009/0278879 A1 | 11/2009 | Takeuchi |
| 2010/0124329 A1 | 5/2010 | Lyman et al. |
| 2014/0078223 A1 | 3/2014 | Ohmura |
| 2014/0320558 A1 | 10/2014 | Ge |
| 2015/0124019 A1 | 5/2015 | Cruz-Uribe |
| 2017/0239944 A1 | 8/2017 | Martin |
| 2017/0242633 A1 | 8/2017 | Martin et al. |
| 2017/0320320 A1 | 11/2017 | Martin et al. |
| 2018/0050537 A1 | 2/2018 | Bakker et al. |
| 2018/0147839 A1 | 5/2018 | Ge |
| 2018/0236761 A1 | 8/2018 | Taniguchi |
| 2018/0236762 A1 | 8/2018 | Negishi |
| 2018/0288276 A1 | 10/2018 | Sato |
| 2021/0206164 A1 | 7/2021 | Gardner |
| 2021/0213731 A1 | 7/2021 | Linn |
| 2021/0221120 A1 | 7/2021 | Linn |

FOREIGN PATENT DOCUMENTS

| | | |
|---|---|---|
| CN | 101092076 A | 12/2007 |
| CN | 107206816 A | 9/2017 |
| EP | 0972374 | 1/2000 |
| EP | 1212197 B1 | 11/2006 |
| JP | H02208052 A | 8/1990 |
| JP | 2004-282330 A | 10/2004 |
| JP | 2004-343468 A | 12/2004 |
| JP | 2005-205770 A | 8/2005 |
| JP | 2007-525342 A | 9/2007 |
| JP | 2009-292148 A | 12/2009 |
| JP | 2011-075387 A | 4/2011 |
| JP | 2016165822 A | 9/2016 |
| JP | 2018-505077 A | 2/2018 |
| TW | 200533107 A | 10/2005 |
| TW | 201346749 A | 11/2013 |
| TW | 201601509 A | 1/2016 |
| WO | 99/40702 A1 | 8/1999 |
| WO | 01/10647 A1 | 2/2001 |
| WO | WO-2016089371 A1 | 6/2016 |
| WO | WO-2016130157 A1 | 8/2016 |
| WO | WO-2017180142 A1 | 10/2017 |
| WO | WO-2018071034 A1 | 4/2018 |
| WO | WO-2018080479 A1 | 5/2018 |
| WO | WO-2018080480 A1 | 5/2018 |
| WO | WO-2018190855 A1 | 10/2018 |
| WO | WO-2019009902 A1 | 1/2019 |
| WO | WO-2019017951 A1 | 1/2019 |

OTHER PUBLICATIONS

"What is a Kelvin connection and when should it be used?" Jan. 2019 (2 pages).

"Four-Terminal Sensing." Wikipedia: The Free Encyclopedia. Wikimedia Foundation, Inc. Sep. 16, 2018 (3 pages).

* cited by examiner

IDENTIFYING RANDOM BITS IN CONTROL DATA PACKETS

CROSS-REFERENCE TO RELATED APPLICATIONS

This application is a U.S. National Stage Application of PCT Application No. PCT/US2019/016739, filed Feb. 6, 2019, entitled "IDENTIFYING RANDOM BITS IN CONTROL DATA PACKETS."

BACKGROUND

Many printing devices include at least one fluid ejection device (e.g., print head) designed to house cartridges filled with fluid (e.g., ink or toner in the case of an inkjet printing device, or a detailing agent in the case of a three dimensional printing device). The fluid ejection devices further include at least one nozzle via which the fluid is dispensed from the cartridges onto a substrate (e.g., paper). When printing a document, the print engine controller of the printing device may send commands to the fluid ejection devices that control when the individual nozzles of the fluid ejection devices "fire" or dispense fluid.

DETAILED DESCRIPTION

Figure 1:
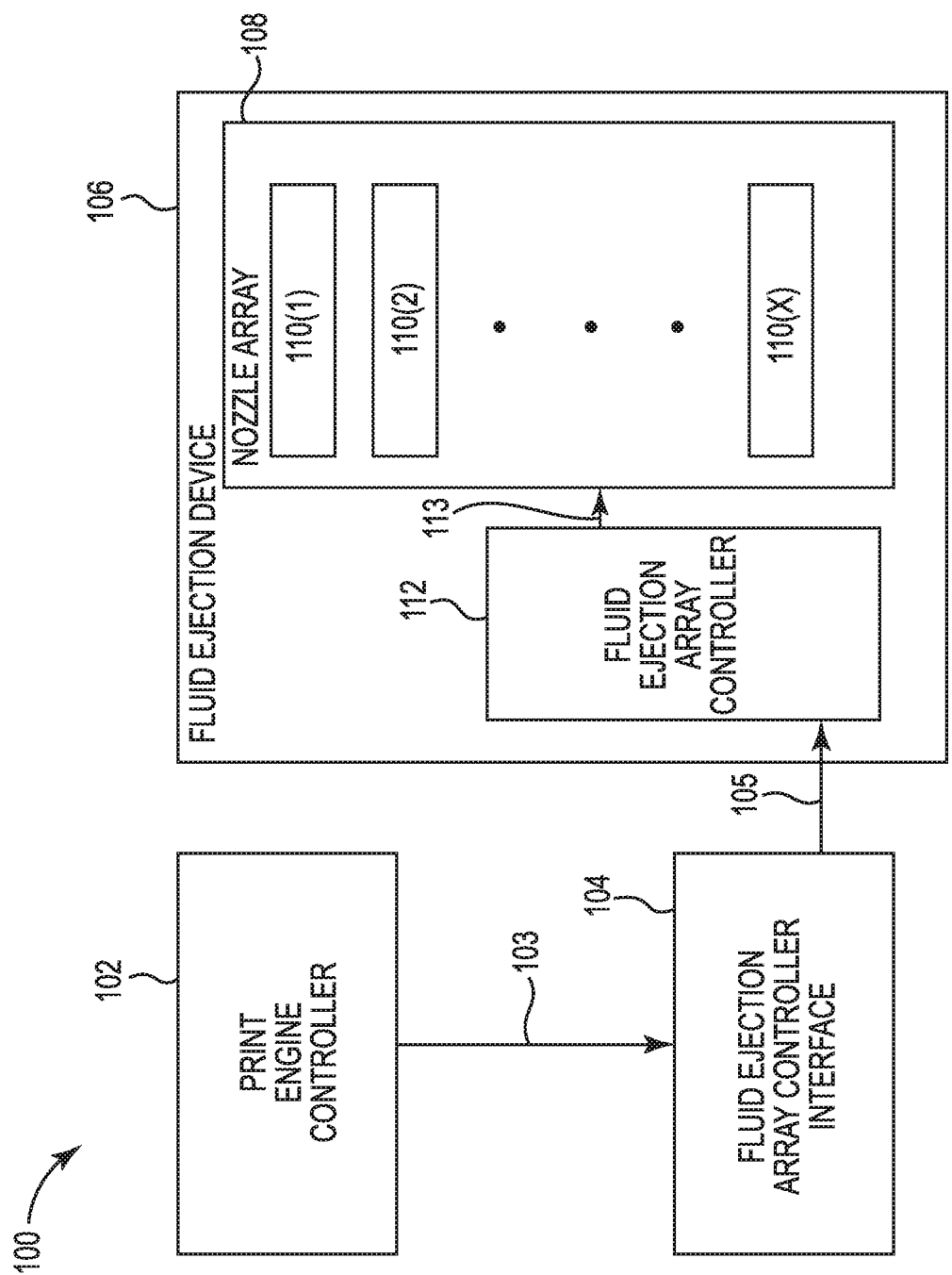
FIG. 1 is a block diagram illustrating elements of a printing device according to one example.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

When printing a document, a print engine controller of a printing device may send commands in control data packets to the fluid ejection devices (e.g., print heads), via a data path, that control when the individual nozzles of the fluid ejection devices "fire" or dispense fluid (e.g., ink, toner in the case of an inkjet printing device, or a detailing agent in the case of a three dimensional printing device). For high-density print applications, the various nozzles may be grouped into a plurality of "primitives," such that one nozzle in each primitive fires at any given time based on the data loaded from the print engine controller (e.g., one bit of data per primitive). For lower density print applications, a plurality of primitives may be combined to form a "virtual" primitive in which one nozzle in each virtual primitive fires at any given time (thus, some primitives in the virtual primitive may not fire any nozzles).

Some shift register fluid ejection implementations may allow the insertion of random data in the header of a control data packet. A variable number of random data bits may be added to the header. The random data bits may have no functional impact on real nozzle data and/or control word data, but can provide benefits such as identifying data integrity issues and effectively randomizing or dithering the fire period to spread the frequency of fire-related electromagnetic compatibility emissions. However, some fluid ejection device designs may not utilize a receiver that is compatible with random length headers. These fluid ejection device designs may not operate properly in systems where random length headers are utilized. For example, some fluid ejection device designs may utilize a different control word or datapath structure, so a remapping of bits within the data packet may be performed to provide compatibility. Such a remapping involves a capability to align to the random length header to determine the location of the true control word/data packet.

Some examples of the present disclosure are directed to a fluid ejection array controller interface that determines the location of random data within a control data packet. Alignment to the random length header allows removal of the random header and/or modification of the data packet (including the control word). Some examples of the present disclosure are directed to a fluid ejection array controller interface that removes randomly inserted bits from the header of a control data packet before the control data packet is provided to the fluid ejection device. Some examples disclosed herein allow a system defined for compatibility with a shift register fluid ejection implementation to be used with alternative fluid ejection devices (e.g., by removing the random header), or a system defined for a specific control word bit ordering (e.g., address bit locations) to be used with alternative fluid ejection devices (e.g., by modifying the control word data and/or bit mapping to rearrange the control word bits). Some examples provide a flexible system design for future, undefined fluid ejection architectures.

In one example, control data packets and an input clock signal are received by the fluid ejection array controller interface, and the randomly inserted bits are removed. The fluid ejection array controller interface buffers the modified control data packets without the randomly inserted bits. The fluid ejection array controller interface outputs the buffered modified control data packets to the fluid ejection device using an independent internal clock that is faster than or equal to the received input clock, which limits buffering of data to a single fire group of data at a time. The independent time base of the internal clock enables the interface to modify the clock timing and data burst length. One example of the fluid ejection array controller interface includes an input shift register, an output shift register, and an internal clock signal generator.

Although examples of the disclosure may be discussed within the context of inkjet printing, the techniques disclosed herein may be further applied to control the fluid ejection devices of three dimensional printing devices and other devices that eject fluid such as ink, toner, or the like, or detailing agents (e.g., binder materials, powders, or the like) used in additive manufacturing processes.

FIG. 1 is a block diagram illustrating elements of a printing device 100 according to one example. Printing device 100 includes a print engine controller 102, a fluid ejection array controller interface 104, and a fluid ejection device 106. In one example, the fluid ejection device 106 may be one of a plurality of fluid ejection devices (e.g., print heads) arranged in a fluid ejection array (e.g., a print bar) of a printing device (e.g., an inkjet printing device or a three dimensional printer). The fluid ejection device 106 includes a nozzle array 108, which further includes nozzle columns 110(1)-110(X) (hereinafter collectively referred to as "nozzle columns 110") arranged in rows along the fluid ejection device 106. Each nozzle column 110 includes a plurality of nozzles arranged to dispense fluid onto a substrate, where the nozzles may be arranged into groups called "primitives." The primitives may be further arranged into groups called "virtual primitives." The number and arrangement of the nozzles may vary depending on the desired print density. The fluid ejection device 106 also includes a fluid ejection array controller 112, which is connected to the nozzle array 108. In some examples, the fluid ejection array controller 112 may also be referred to as a fluid ejection controller, and the fluid ejection array controller interface 104 may also be referred to as a fluid ejection controller interface.

The fluid ejection array controller interface 104 receives control data packets 103 from print engine controller 102 for controlling ejection of fluid by the nozzles of the nozzle array 108. The interface 104 removes randomly inserted bits from the received control data packets 103 to create modified control data packets 105 with the randomly inserted bits removed, and outputs the modified control data packets 105 to the fluid ejection array controller 112. The fluid ejection array controller 112 generates ejection control data 113 for the nozzles of the nozzle array 108 (or, more specifically in some examples, for the virtual primitives of the nozzle array 108) based on the contents of the modified control data packets 105. A data path interconnects the print engine controller 102, the fluid ejection array controller interface 104, and the fluid ejection array controller 112, and transports the control data packets 103 and the modified control data packets 105. The data path may be a high-speed data path, such as a multi-lane serial bus.

In one example, the control data packets 103 are "fire pulse group" (or "FPG") packets containing data about which nozzles of the fluid ejection device 106 should fire. For instance, the control data packets 103 may identify the primitives or virtual primitives containing the nozzles that are to fire, or the packets may contain bits of data for each primitive. One example of a fire pulse group is illustrated in further detail in FIG. 2. The fluid ejection array controller interface 104 removes randomly inserted bits from the received control data packets 103 to create the modified control data packets 105. Based on the information contained in the modified control data packets 105, the fluid ejection array controller 112 writes unique primitive data (e.g., one nozzle's worth of data) to each primitive of the fluid ejection device 106. The unique primitive data is contained in the ejection control data 113. This may involve inserting null values into the control data packets 103 to indicate that a particular primitive should not fire any nozzles.

The fluid ejection array controller 112 may also generate a plurality of nozzle control bits based on the information contained in the modified control data packets 105. The nozzle control bits may include a combination of primitive data, address information, and a FIRE signal local to that primitive. A nozzle control bit instructs an addressed nozzle to fire. In one example, the fluid ejection array controller 112 generates one nozzle control bit for each primitive on the fluid ejection device 106. In one example, the fluid ejection array controller 112 populates the nozzle control bits with bit values (e.g., "0" or "1") that indicate whether a nozzle identified by a corresponding address should fire or not. The fluid ejection array controller 112 may also convey address data to the primitives of the fluid ejection device 106. In one example, the address data identifies (e.g., by corresponding address) which nozzles within the primitives of the fluid ejection device 106 should be fired.

In one example, the fluid ejection array controller interface 104 is implemented as a device that is separate from the fluid ejection device 106 and is positioned between the print engine controller 102 and the fluid ejection device 106. In another example, the fluid ejection array controller interface 104 is integrated into the fluid ejection device 106, and may reside on a common semiconductor die with the fluid ejection array controller 112.

Figure 2:
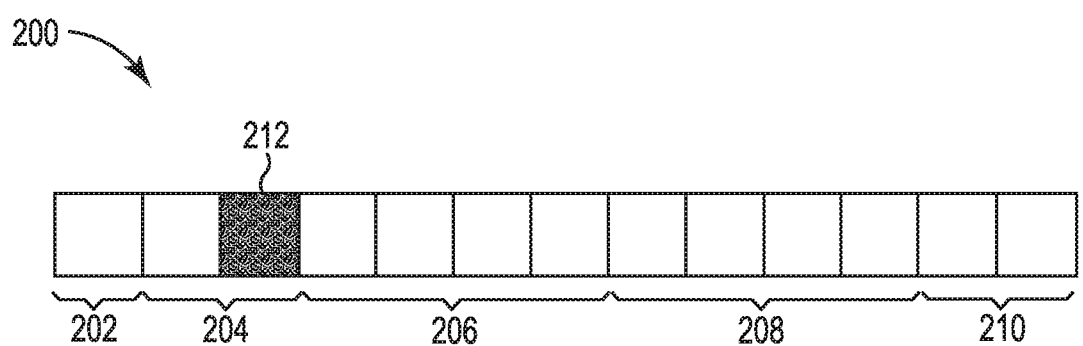
FIG. 2 is a diagram illustrating a control data packet that may be used to communicate commands to fire nozzles of a fluid ejection device according to one example.

FIG. 2 is a diagram illustrating a control data packet 200 that may be used to communicate commands to fire nozzles of a fluid ejection device according to one example. The control data packet 200 is one example of the format of the control data packets 103 (FIG. 1). In one example, the control data packet 200 is a fire pulse group (or FPG) packet. In one example, the control data packet 200 includes random data 202, header 204, a payload comprising a set of address bits 206 and/or a set of fire data bits 208, and a footer 210. The example illustrated in FIG. 2 is an abstraction and is not meant to limit the number of bits that may be included in the packet 200 or in any particular portion of the packet 200.

Random data 202 includes a random number of random data bits added to the front end of the control data packet 200 before the header 204. In one example, the random data 202 is generated by a pseudo-random number generator (PRNG), such as by using a linear feedback shift register approach. The length of the random data 202 (i.e., the number of random data bits included) and the values for the random data bits may both be determined by the PRNG. In one example, the random data 202, having a pseudo-random length, includes 0, 2, 4, 6, or 8 bits of pseudo-random data.

In one example, the header 204 includes bits that are used by the fluid ejection array controller 112 (FIG. 1) to detect the start of the control data packet 200. Thus, the header 204 may include some predefined sequence of bits that indicates the start of a control data packet. In one example, the header 204 additionally includes a set of primitive select bits 212. The primitive select bits 212 may be used, for example, to identify which primitive within a virtual primitive is being addressed (and should, consequently, fire). The primitive select bits 212 may be contained in a different portion of the control data packet 200, such as the payload or the footer 210.

In one example, the set of address bits 206 identifies, for each primitive, an address (also referred to as an "embedded address") corresponding to a nozzle to be fired (i.e., to fire the unique primitive data and eject fluid). In one example, the set of address bits 206 may be omitted from the control data packet 200; in this case, the address bits 206 may be generated by an address generator of the fluid ejection array controller 112.

In one example, the set of fire data bits 208 includes one nozzle's worth of data (e.g., unique primitive data) for each primitive on the fluid ejection device 106. The data included in the set of fire data bits 208 determines whether the nozzle that is identified by the set of address bits within a particular primitive should fire. For instance, the fire data bits 208 may include a non-null value (e.g., "1") to indicate that a nozzle of a primitive should fire. The data included in the set of fire data bits 208 may be different for each primitive.

In one example, the footer 210 comprises bits that are used by the fluid ejection array controller 112 to detect the end of the control data packet 200. Thus, the footer 210 may include some predefined sequence of bits that indicates the end of a control data packet.

Once the control data packet 200 is loaded into the fluid ejection array controller 112, the information bits of data and address are then present at each primitive. It is at this time a fire signal is sent to all primitives (propagated from first to last primitive). This fire signal then generates nozzle control bits, which include a combination of primitive data, address information, and a FIRE signal local to that primitive. The nozzle control bits are then sent to the primitive groups on the fluid ejection device 106, and the primitive groups will fire the nozzles addressed by the nozzle control bits. To fire all of the nozzles on the fluid ejection device 106 in one fire pulse group, a virtual primitive control packet 200 would thus be loaded for every address value.

Figure 3:
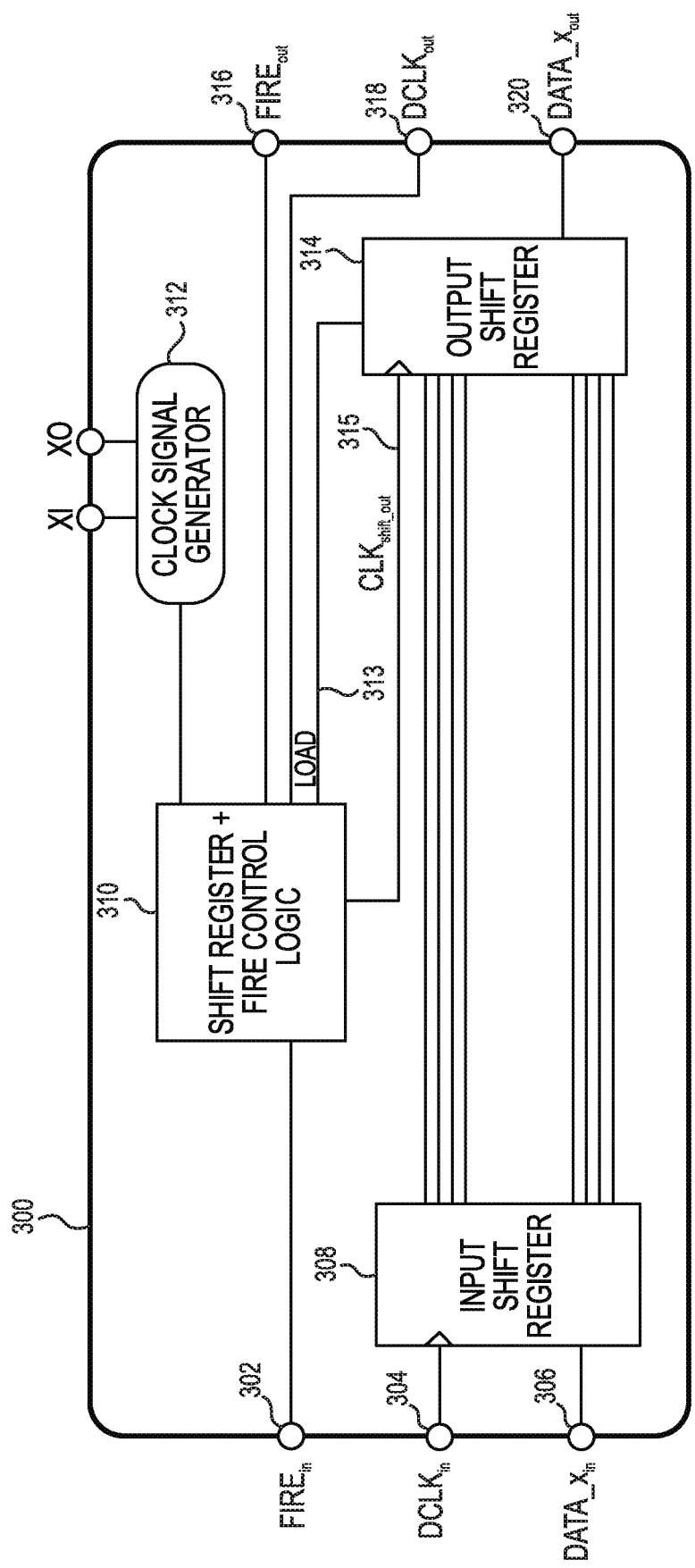
FIG. 3 is a block diagram illustrating a fluid ejection array controller interface according to one example.

FIG. 3 is a block diagram illustrating a fluid ejection array controller interface 300 according to one example. The interface 300 shown in FIG. 3 is one example implementation of the interface 104 shown in FIG. 1. The interface 300 includes $FIRE_{in}$ input 302, $DCLK_{in}$ input 304, $DATA\_x_{in}$ input 306, input shift register 308, shift register and fire control logic 310, clock signal generator 312, output shift register 314, $FIRE_{out}$ output 316, $DCLK_{out}$ output 318, and $DATA\_x_{out}$ output 320. In one example, the input shift register 308 and the output shift register 314 are fixed-length shift registers that have the same length. The clock signal generator 312 may be a phase locked loop or a digitally controlled oscillator. FIG. 3 is described in further detail below with additional reference to FIG. 4.

Figure 4:
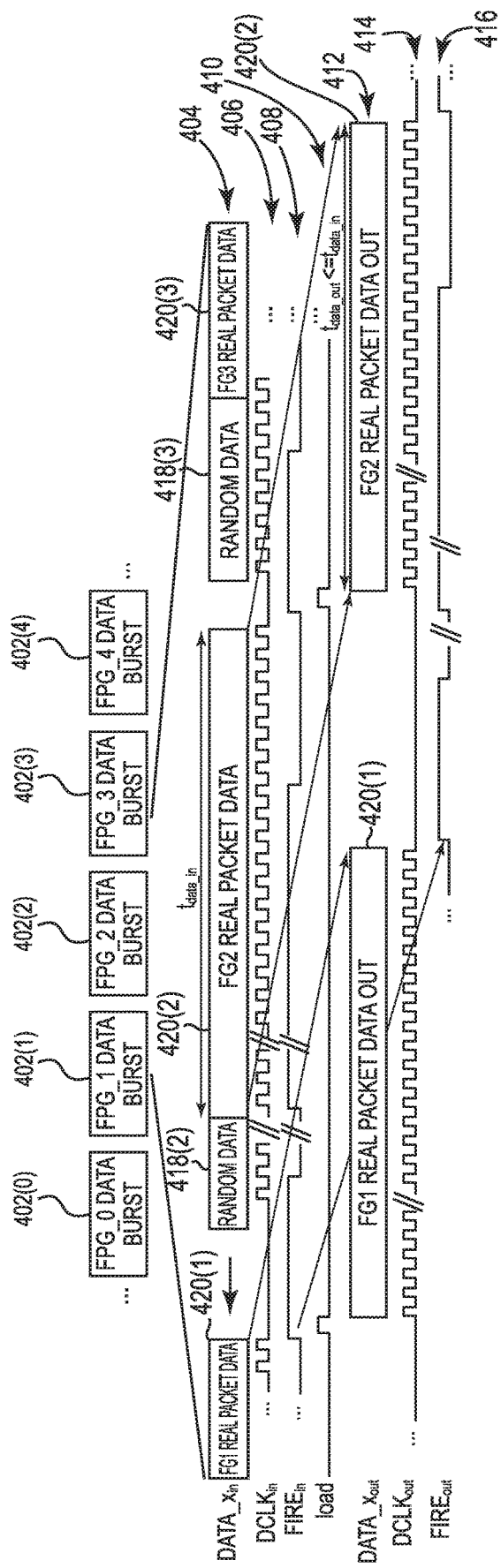
FIG. 4 is a timing diagram illustrating the timing for signals of the fluid ejection array controller interface shown in FIG. 3 according to one example.

FIG. 4 is a timing diagram illustrating the timing for signals of the fluid ejection array controller interface 300 shown in FIG. 3 according to one example. FIG. 4 shows five control data packets 402(0)-402(4) (collectively referred to herein as control data packets 402). In one example, the control data packets 402 are "fire pulse group" (or "FPG") packets or data bursts containing data about which nozzles of the fluid ejection device should fire. Each of the control data packets 402 includes real packet data (e.g., real packet data 420(1), 420(2), and 420(3)) and random data (e.g., random data 418(2) and 418(3)).

FIG. 4 also shows signals 404, 406, 408, 410, 412, 414, and 416. $DATA\_x_{in}$ signal 404 represents control data packets 402 received by the interface 300 via input 306 and provided in a serial manner to the input shift register 308. $DCLK_{in}$ signal 406 represents an input clock signal received by the interface 300 via input 304 and provided to the input shift register 308 to control the clocking of the input shift register 308. $FIRE_{in}$ signal 408 represents a fire signal received by the interface 300 via input 302 and provided to shift register and fire control logic 310. Load signal 410 is a control signal generated by shift register and fire control logic 310 and provided to output shift register 314 via communication link 313. $DATA\_x_{out}$ signal 412 represents the real packet data (e.g., real packet data 420(1), 420(2), and 420(3)) output by output shift register 314 to output 320.

The real packet data for each control data packet that is output by output shift register 314 may also be referred to herein as a modified control data packet. $DCLK_{out}$ signal 414 represents an output clock signal that is output by shift register and fire control logic 310 to output 318 of interface 300. $FIRE_{out}$ signal 416 represents a control signal that is output by shift register and fire control logic 310 to output 316 of interface 300.

In one example, inputs 302, 304, and 306 are connected to a print engine controller (e.g., print engine controller 102), and outputs 316, 318, and 320 are connected to a fluid ejection array controller (e.g., fluid ejection array controller 112). In operation according to one example, a control data packet 402 is received in a serial manner by input shift register 308 via input 306. In one example, the input shift register 308 is a fixed-length shift register, with the length of the shift register being defined to be equal to the length of the real packet data (e.g., real packet data 420(1), 420(2), or 420(3)). This results in the random length header of random data (e.g., random data 418(2) or 418(3)) rolling off the end of the input shift register 308 and being discarded.

The retained real packet data in the input shift register 308 is parallel loaded to the output shift register 314 at the end of each packet. The real packet data in the output shift register 314 is serially driven to the fluid ejection device (e.g., fluid ejection device 106) via output 320. The output shift register 314 is clocked by an internal clock signal, $clk_{shift\_out}$, which is output from the shift register and fire control logic 310 via communication link 315. The internal clock signal, $clk_{shift\_out}$, is generated by the shift register and fire control logic 310 based on a clock signal provided by the clock signal generator 312. In one example, the internal clock signal, $clk_{shift\_out}$, is faster than the $DCLK_{in}$ signal 406. The input shift register 308 may continue loading input data while the output shift register 314 is simultaneously being utilized to re-drive real packet data.

The $FIRE_{in}$ signal 408 received via input 302 is timed via an internal counter in shift register and fire control logic 310. The $FIRE_{out}$ signal 416 output by shift register and fire control logic 310 via output 316 is delayed to the end of the $DATA\_x_{out}$ packet) and re-driven to emulate the input timing (e.g., pulse widths, deadtime, etc.).

Figure 5:
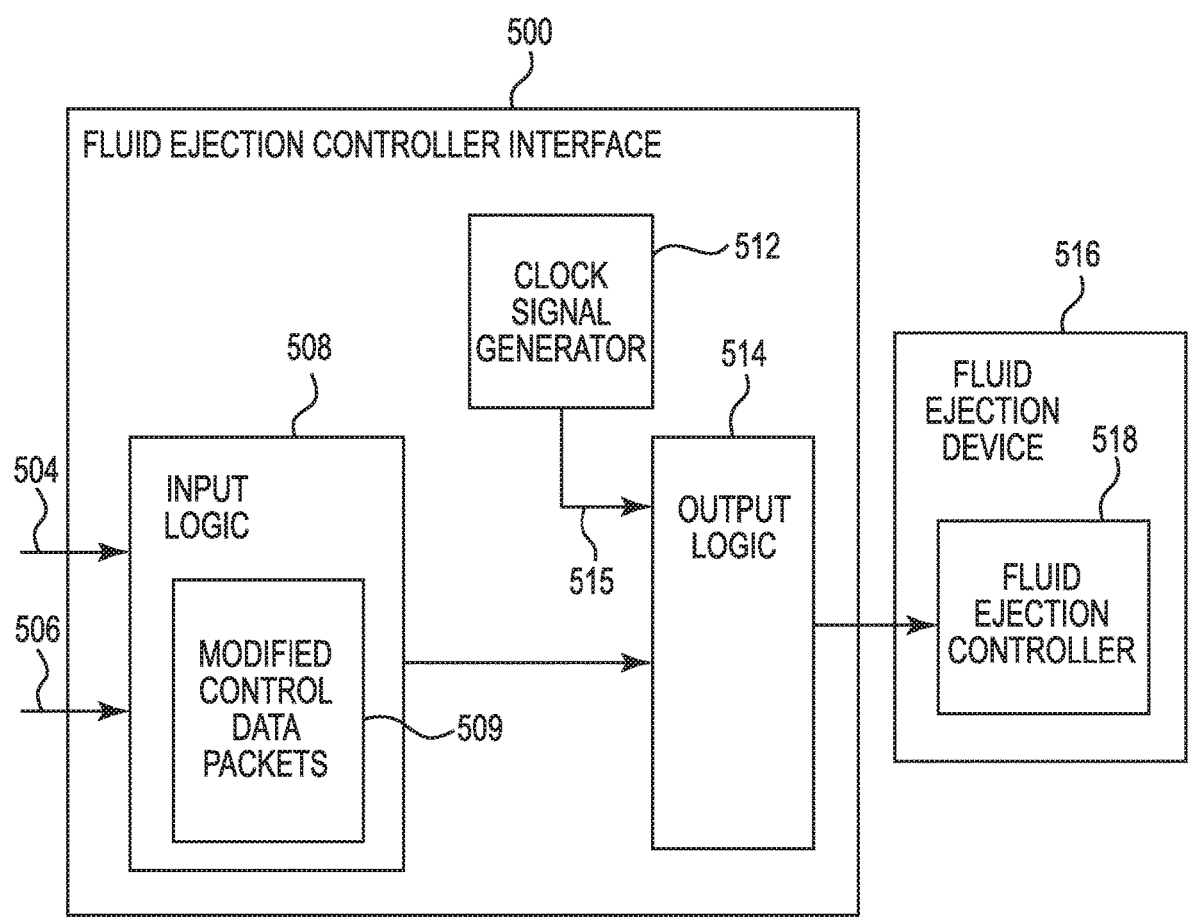
FIG. 5 is a block diagram illustrating an example of a fluid ejection controller interface.

One example of the present disclosure is directed to a fluid ejection controller interface. FIG. 5 is a block diagram illustrating an example of a fluid ejection controller interface 500. The fluid ejection controller interface 500 includes input logic 508 to receive control data packets 506 and a first clock signal 504. Each control data packet 506 includes a set of primitive data bits and a set of random bits. The input logic 508 identifies the random bits in the received control data packets 506 to facilitate the creation of modified control data packets 509.

The fluid ejection controller interface 500 includes a clock signal generator 512 to generate a second clock signal 515 that is different than the first clock signal 504. The fluid ejection controller interface 500 includes output logic 514 to receive the modified control data packets 509, and output the modified control data packets 509 to a fluid ejection controller 518 of a fluid ejection device 516 based on the second clock signal 515.

The set of random bits for each control data packet 506 may have a pseudo-random length. Values for the set of random bits for each control data packet 506 may have pseudo-random number values. The second clock signal 514 may be faster than or equal to the first clock signal 504. The input logic 508 may comprise an input shift register, and the output logic 514 may comprise an output shift register. The input shift register and the output shift register may be fixed-length shift registers having the same length. The fluid ejection controller interface 500 may further include control logic to receive fire signals, and control the output logic. The fluid ejection controller interface 500 may be implemented separate from the fluid ejection device 516. The fluid ejection controller interface 500 may be integrated into the fluid ejection device 516. The fluid ejection controller interface 500 may reside on a common semiconductor die with the fluid ejection controller 518. The input logic may remove the random bits from the received control data packets 506 to facilitate the creation of the modified control data packets 509. The fluid ejection controller interface 500 may further include modification logic to modify at least one of positions or values of bits in the received control data packets to facilitate the creation of the modified control data packets.

Figure 6:
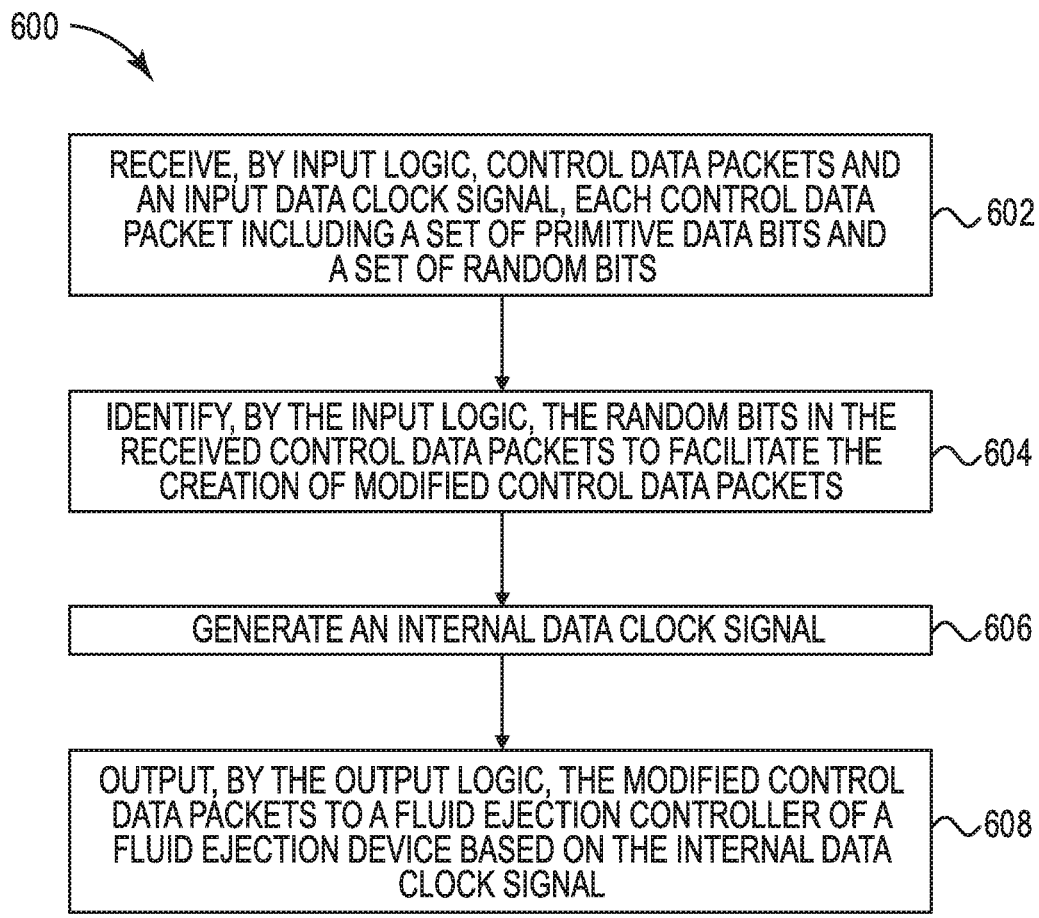
FIG. 6 is a flow diagram illustrating a method of processing control data packets according to one example.

Another example of the present disclosure is directed to a method of processing control data packets. FIG. 6 is a flow diagram illustrating a method 600 of processing control data packets according to one example. At 602, the method 600 includes receiving, by input logic, control data packets and an input data clock signal, each control data packet including a set of primitive data bits and a set of random bits. At 604, the method 600 includes identifying, by the input logic, the random bits in the received control data packets to facilitate the creation of modified control data packets. At 606, the method 600 includes generating an internal data clock signal. At 608, the method 600 includes outputting, by the output logic, the modified control data packets to a fluid ejection controller of a fluid ejection device based on the internal data clock signal.

The set of random bits for each control data packet in method 600 may have a pseudo-random length, and the values for the set of random bits for each control data packet may be pseudo-random number values. The method 600 may further include receiving, by control logic, fire signals; and controlling, by the control logic, the output logic based on the received fire signals and the internal data clock signal. The method 600 may further include removing, by the input logic, the random bits from the received control data packets to facilitate the creation of the modified control data packets. The method 600 may further include modifying, by modification logic, at least one of positions or values of bits in the received control data packets to facilitate the creation of the modified control data packets.

Yet another example of the present disclosure is directed to an apparatus, which includes an input shift register to serially receive control data packets and an input data clock signal. Each control data packet includes a set of primitive data bits and a set of random bits. The set of random bits for each control data packet has a pseudo-random length. The apparatus includes modification logic to modify at least one of positions or values of bits in the received control data packets to facilitate the creation of the modified control data packets. The apparatus includes a clock signal generator to generate an internal data clock signal that is faster than or equal to the input data clock signal. The apparatus includes an output shift register to receive the modified control data packets, and output the modified control data packets to a fluid ejection controller of a fluid ejection device based on the input data clock signal.

The apparatus may further include control logic to receive fire signals and control the output shift register based on the received fire signals and the internal data clock signal. The input shift register may discard the random bits from the received control data packets to facilitate the creation of the modified control data packets.

Figure 7:
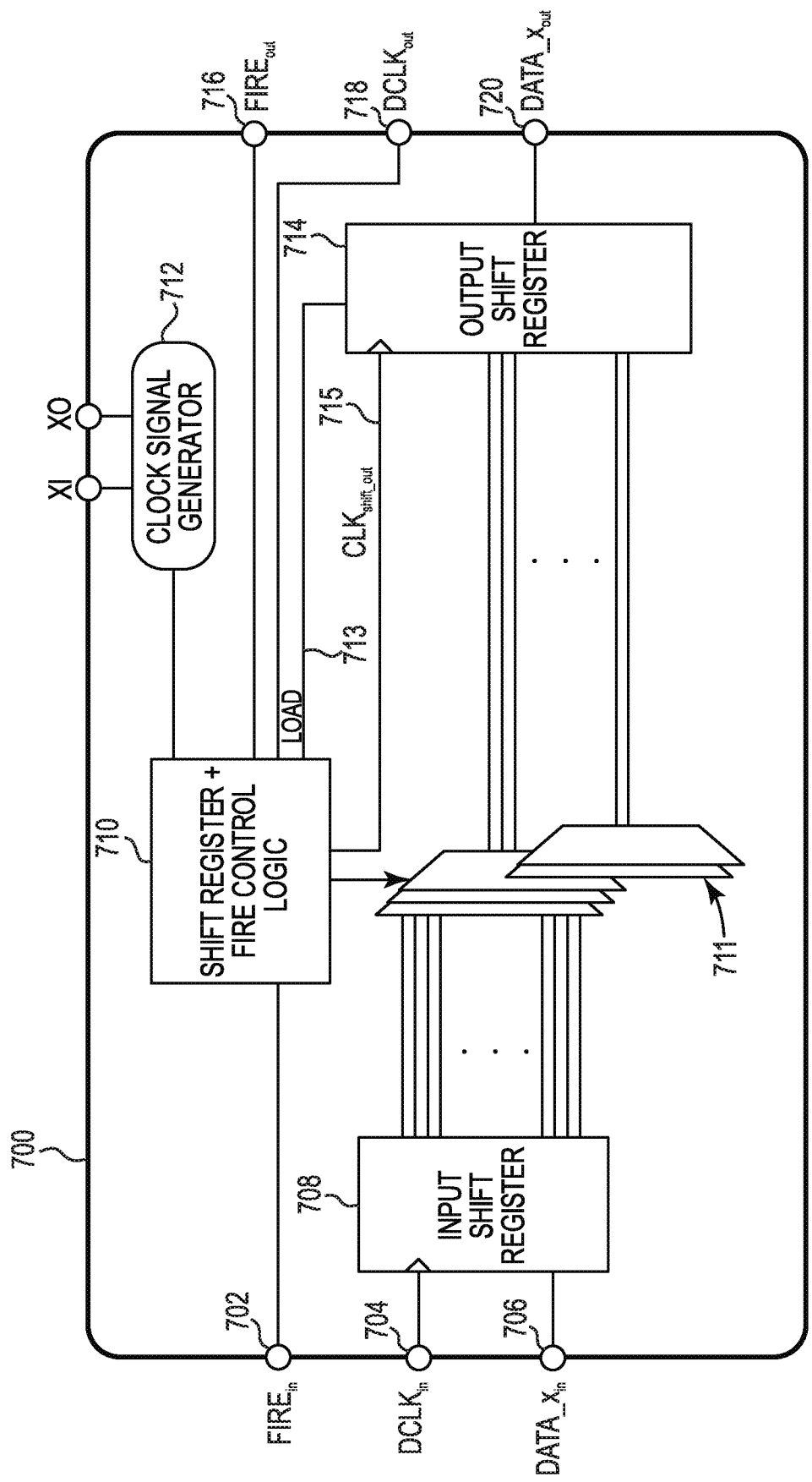
FIG. 7 is a block diagram illustrating a fluid ejection array controller interface according to another example.

FIG. 7 is a block diagram illustrating a fluid ejection array controller interface 700 according to another example. The interface 700 shown in FIG. 7 is one example implementation of the interface 104 shown in FIG. 1. The interface 700 includes $FIRE_{in}$ input 702, $DCLK_{in}$ input 704, $DATA\_x_{in}$ input 706, input shift register 708, shift register and fire control logic 710, rearrangement and modification logic 711, clock signal generator 712, output shift register 714, $FIRE_{out}$ output 716, $DCLK_{out}$ output 718, and $DATA\_x_{out}$ output 720. In one example, the input shift register 708 and the output shift register 714 are fixed-length shift registers that have the same length. The clock signal generator 712 may be a phase locked loop or a digitally controlled oscillator. FIG. 7 is described in further detail below with additional reference to FIG. 8.

Figure 8:
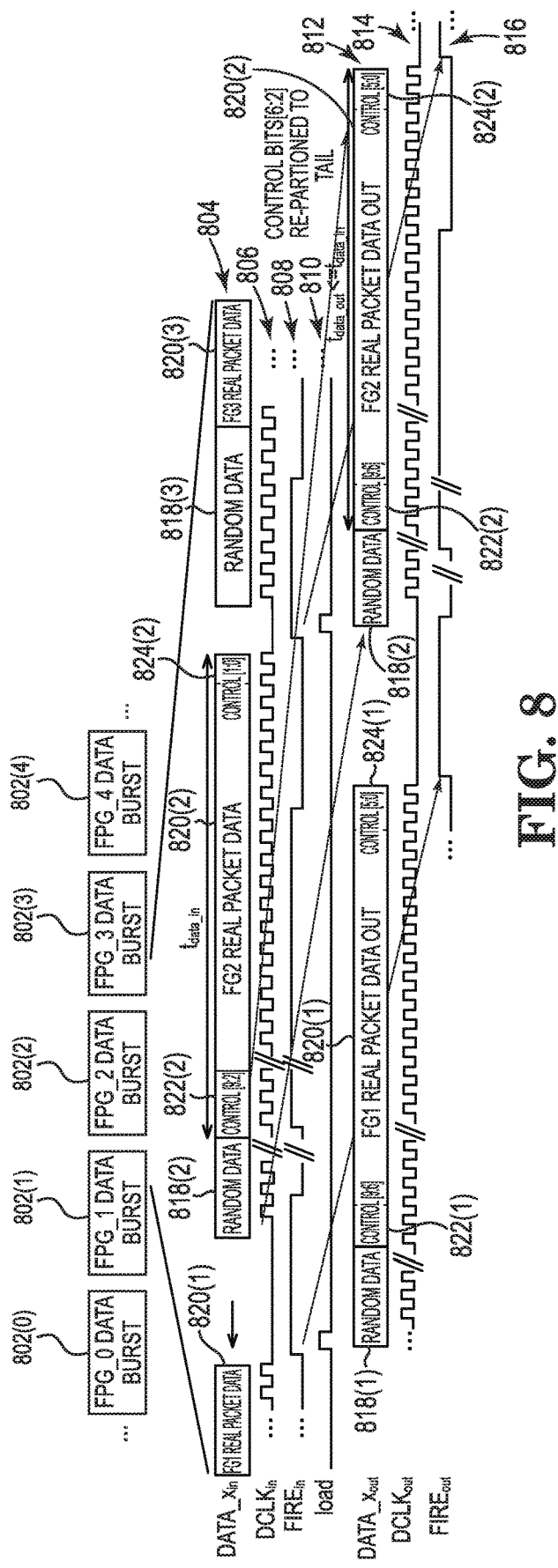
FIG. 8 is a timing diagram illustrating the timing for signals of the fluid ejection array controller interface shown in FIG. 7 according to one example.

FIG. 8 is a timing diagram illustrating the timing for signals of the fluid ejection array controller interface 700 shown in FIG. 7 according to one example. FIG. 8 shows five control data packets 802(0)-802(4) (collectively referred to herein as control data packets 802). In one example, the control data packets 802 are "fire pulse group" (or "FPG") packets or data bursts containing data about which nozzles of the fluid ejection device should fire. Each of the control data packets 802 includes real packet data (e.g., real packet data 820(1), 820(2), and 820(3)) and random data (e.g., random data 818(2) and 818(3)).

FIG. 8 also shows signals 804, 806, 808, 810, 812, 814, and 816. $DATA\_x_{in}$ signal 804 represents control data packets 802 received by the interface 700 via input 706 and provided in a serial manner to the input shift register 708. $DCLK_{in}$ signal 806 represents an input clock signal received by the interface 700 via input 704 and provided to the input shift register 708 to control the clocking of the input shift register 708. $FIRE_{in}$ signal 808 represents a fire signal received by the interface 700 via input 702 and provided to shift register and fire control logic 710. Load signal 810 is a control signal generated by shift register and fire control logic 710 and provided to output shift register 714 via communication link 713. $DATA\_x_{out}$ signal 812 represents the packet data output by output shift register 714 to output 720. The packet data for each received control data packet that is output by output shift register 714 may or may not include the received random data, and may also be referred to herein as a modified control data packet. $DCLK_{out}$ signal 814 represents an output clock signal that is output by shift register and fire control logic 710 to output 718 of interface 700. $FIRE_{out}$ signal 816 represents a control signal that is output by shift register and fire control logic 710 to output 716 of interface 700.

In one example, inputs 702, 704, and 706 are connected to a print engine controller (e.g., print engine controller 102), and outputs 716, 718, and 720 are connected to a fluid ejection array controller (e.g., fluid ejection array controller 112). In operation according to one example, a control data packet 802 is received in a serial manner by input shift register 708 via input 706. In one example, the input shift register 708 is a fixed-length shift register, with the length of the shift register being defined to be equal to either the length of the real packet data (e.g., real packet data 820(1), 820(2), or 820(3)), or the length of the entire control data packet 802. For examples in which the input shift register 708 has a length that is equal to the length of the real packet data, the random length header of random data (e.g., random data 818(1), 818(2), or 818(3)) rolls off the end of the input shift register 708 and may be discarded.

The retained data in the input shift register 708 is parallel loaded to the output shift register 714 at the end of each packet. Rearrangement and modification logic 711 may include steering multiplexers to rearrange the bit ordering (e.g., to rearrange bits in the control word), and may include additional logic to apply additional modifications to bits within the control word (e.g., changing the values of particular bits). The data in the output shift register 714 is serially driven to the fluid ejection device (e.g., fluid ejection device 106) via output 720. The output shift register 714 is clocked by an internal clock signal, $clk_{shift\_out}$, which is output from the shift register and fire control logic 710 via communication link 715. The internal clock signal, $clk_{shift\_out}$, is generated by the shift register and fire control logic 710 based on a clock signal provided by the clock signal generator 712. In one example, the internal clock signal, $clk_{shift\_out}$, is faster than the $DCLK_{in}$ signal 806. The input shift register 708 may continue loading input data while the output shift register 714 is simultaneously being utilized to re-drive packet data. In examples in which random data is re-driven by interface 700, the shift register and fire control logic 710 may be used to count incoming data packet bits and clock out an equal number of bits from the output shift register 714.

The $FIRE_{in}$ signal 808 received via input 702 is timed via an internal counter in shift register and fire control logic 710. The $FIRE_{out}$ signal 816 output by shift register and fire control logic 710 via output 716 is delayed to the end of the $DATA_{xout}$ packet) and re-driven to emulate the input timing (e.g., pulse widths, deadtime, etc.).

In the example shown in FIG. 8, each of the control data packets 802 includes a control word, which includes control word bits [9:2] contained at the head (e.g., head 822(2)) of the real packet data, and includes control word bits [1:0] contained at the tail (e.g., tail 824(2)) of the real packet data. Rearrangement and modification logic 711 is used to repartition the control word in each of the received control data packets 802. In the illustrated example, logic 711 moves control word bits [5:2] from the head of the real packet data to the tail of the real packet data. As shown in FIG. 8, after the repartitioning, the real packet data in the $DATA_{xout}$ signal 812 includes heads 822(1) and 822(2) that include control word bits [9:6], and tails 824(1) and 824(2) that include control word bits [0:5]. The repartitioning shown in FIG. 8 is one example of the modifications that may be performed by interface 700. Other examples may involve other modifications to the received data, including a different control word partitioning, data bit reordering, and modifying data bit values.

Aspects of the present disclosure can be implemented by machine readable instructions and/or in a combination of machine readable instructions and hardware, e.g., using application specific integrated circuits (ASIC), a programmable logic array (PLA), including a field-programmable gate array (FPGA), or a state machine deployed on a hardware device, a general purpose computer or any other hardware equivalents, e.g., computer readable instructions pertaining to the method(s) discussed herein can be used to configure a hardware processor to perform the blocks, functions and/or operations of the disclosed methods.

Furthermore, when a hardware processor executes instructions to perform "operations", this could include the hardware processor performing the operations directly and/or facilitating, directing, or cooperating with another hardware device or component, e.g., a co-processor and the like, to perform the operations. The processor executing the machine readable instructions relating to method(s) described herein can be perceived as a programmed processor or a specialized processor. As such, modules for controlling devices disclosed herein, including associated data structures, of the present disclosure can be stored on a tangible or physical (broadly non-transitory) computer-readable storage device or medium, e.g., volatile memory, non-volatile memory, ROM memory, RAM memory, magnetic or optical drive, device or diskette and the like. More specifically, the computer-readable storage device may comprise any physical devices that provide the ability to store information such as data and/or instructions to be accessed by a processor or a computing device such as a computer or an application server.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A fluid ejection controller interface, comprising:
   input logic to receive control data packets and a first clock signal, each control data packet including a set of primitive data bits and a set of random bits, wherein the input logic identifies the random bits in the received control data packets to facilitate the creation of modified control data packets;
   a clock signal generator to generate a second clock signal that is different than the first clock signal; and
   output logic to receive the modified control data packets, and output the modified control data packets to a fluid ejection controller of a fluid ejection device based on the second clock signal.

2. The fluid ejection controller interface of claim 1, wherein the set of random bits for each control data packet has a pseudo-random length.

3. The fluid ejection controller interface of claim 1, wherein values for the set of random bits for each control data packet are pseudo-random number values.

4. The fluid ejection controller interface of claim 1, wherein the second clock signal is faster than or equal to the first clock signal.

5. The fluid ejection controller interface of claim 1, wherein the input logic comprises an input shift register, and wherein the output logic comprises an output shift register.

6. The fluid ejection controller interface of claim 5, wherein the input shift register and the output shift register are fixed-length shift registers having the same length.

7. The fluid ejection controller interface of claim 1, and further comprising control logic to receive fire signals, and control the output logic.

8. The fluid ejection controller interface of claim 1, wherein the fluid ejection controller interface is implemented separate from the fluid ejection device.

9. The fluid ejection controller interface of claim 1, wherein the fluid ejection controller interface is integrated into the fluid ejection device.

10. The fluid ejection controller interface of claim 9, wherein the fluid ejection controller interface resides on a common semiconductor die with the fluid ejection controller.

11. The fluid ejection controller interface of claim 1, wherein the input logic removes the random bits from the received control data packets to facilitate the creation of the modified control data packets.

12. The fluid ejection controller interface of claim 1, and further comprising:
modification logic to modify at least one of positions or values of bits in the received control data packets to facilitate the creation of the modified control data packets.

13. A method, comprising:
receiving, by input logic, control data packets and an input data clock signal, each control data packet including a set of primitive data bits and a set of random bits;
identifying, by the input logic, the random bits in the received control data packets to facilitate the creation of modified control data packets;
generating an internal data clock signal; and
outputting, by the output logic, the modified control data packets to a fluid ejection controller of a fluid ejection device based on the internal data clock signal.

14. The method of claim 13, wherein the set of random bits for each control data packet has a pseudo-random length, and wherein values for the set of random bits for each control data packet are pseudo-random number values.

15. The method of claim 13, and further comprising:
receiving, by control logic, fire signals; and
controlling, by the control logic, the output logic based on the received fire signals and the internal data clock signal.

16. The method of claim 13, and further comprising:
removing, by the input logic, the random bits from the received control data packets to facilitate the creation of the modified control data packets.

17. The method of claim 13, and further comprising:
modifying, by modification logic, at least one of positions or values of bits in the received control data packets to facilitate the creation of the modified control data packets.

18. An apparatus, comprising:
an input shift register to serially receive control data packets and an input data clock signal, each control data packet including a set of primitive data bits and a set of random bits, wherein the set of random bits for each control data packet has a pseudo-random length;
modification logic to modify at least one of positions or values of bits in the received control data packets to facilitate the creation of the modified control data packets;
a clock signal generator to generate an internal data clock signal that is faster than or equal to the input data clock signal; and
an output shift register to receive the modified control data packets, and output the modified control data packets to a fluid ejection controller of a fluid ejection device based on the input data clock signal.

19. The apparatus of claim 18, and further comprising control logic to receive fire signals and control the output shift register based on the received fire signals and the internal data clock signal.

20. The apparatus of claim 18, wherein the input shift register discards the random bits from the received control data packets to facilitate the creation of the modified control data packets.

* * * * *